(12) United States Patent
Ducreé et al.

(10) Patent No.: US 7,418,977 B2
(45) Date of Patent: Sep. 2, 2008

(54) LIQUID-HANDLING APPARATUS HAVING A LIQUID SWITCH AND METHOD FOR HANDLING LIQUIDS

(75) Inventors: Jens Ducreé, Freiburg (DE); Roland Zengerle, Waldkirch (DE); Thilo Brenner, Wilnsdorf (DE); Thomas Glatzel, Trebur (DE)

(73) Assignee: Albert-Ludwigs-Universitaet, Freiburg (DE)

( * ) Notice: Subject to any disclaimer, the term of this patent is extended or adjusted under 35 U.S.C. 154(b) by 281 days.

(21) Appl. No.: 10/957,950

(22) Filed: Oct. 4, 2004

(65) Prior Publication Data

US 2006/0073082 A1    Apr. 6, 2006

(51) Int. Cl.
*F15C 1/04* (2006.01)

(52) U.S. Cl. ....................... 137/825; 210/651
(58) Field of Classification Search ......... 137/825–828; 435/6, 287.2; 210/651, 806, 321.6
See application file for complete search history.

(56) References Cited

U.S. PATENT DOCUMENTS

| 4,469,793 A | 9/1984 | Guigan |
| 5,610,074 A | 3/1997 | Beritashvili et al. |
| 2003/0146155 A1* | 8/2003 | Tooke et al. ............. 210/651 |

2005/0126312 A1*  6/2005  Bedingham et al. ...... 73/863.01

OTHER PUBLICATIONS

Brenner et al., "A Flow Switch Based on Coriolis Force", 7th International Conference on Minaturized Chemical and Biochemical Analysis, Oct. 5-9, 2003, pp. 903-906.
Duffy et al., "Rapid Prototyping of Microfluidic Switches in Poly (Dimethyl Siloxane) and Their Actuation by Electro-Osmotic Flow", J. Micromech. Microeng., 1999, pp. 217-217, United Kingdom.
Felton, Michael K., "CD Simplicity", Analytical Chemistry, pp. 302-306, Jul. 1, 2003.
Madou et al., "The LabCD(TM): A Centrigue-Based Microfluidic Platform for Diagnostics", SPIE, pp. 80-93, vol. 3259; Apr. 10, 1998.
Schembri et al., "Centrifugation and Capillarity Integrated Into a Multiple Analyte Whole Blood Analyser", Journal of Automatic Chemistry, May-Jun. 1995, pp. 99-104, vol. 17, No. 3.

* cited by examiner

*Primary Examiner*—John Rivell
*Assistant Examiner*—Cloud K Lee
(74) *Attorney, Agent, or Firm*—Michael A. Glenn; Glenn Patent Group

(57) ABSTRACT

A liquid-handling apparatus has a liquid switch, which has a first channel branching into a second and a third channel, wherein the channels are formed in a rotation body. The channels are adapted to route a liquid volume from the first channel into one of the second channel and the third channel dependent on whether a Coriolis force and/or an Euler force prevails a centrifugal force or not. A liquid-handling apparatus having such a liquid switch is particularly suited for applications in which different volumes of liquid have to be passed through a stationary phase.

44 Claims, 9 Drawing Sheets

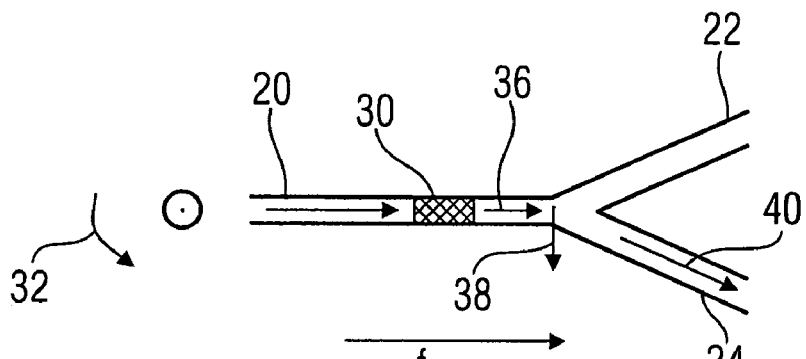
FIG. 3a
FIG. 3b
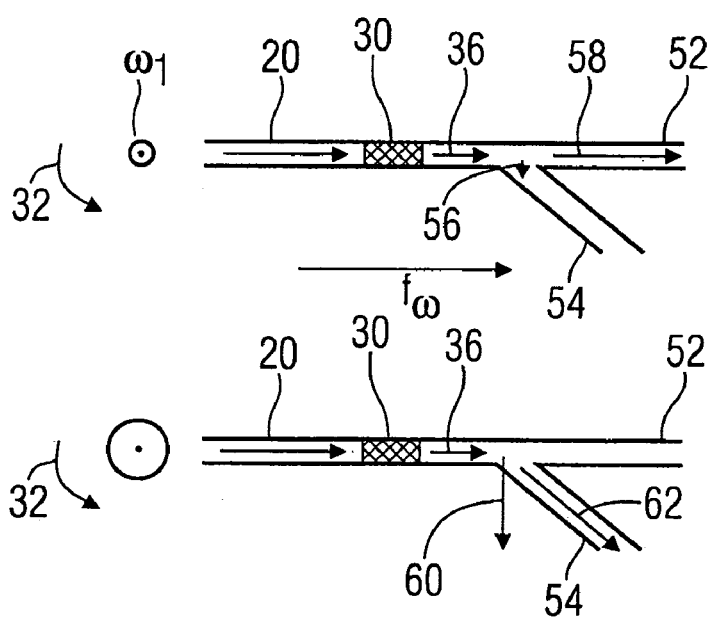
FIG. 4a
FIG. 4b

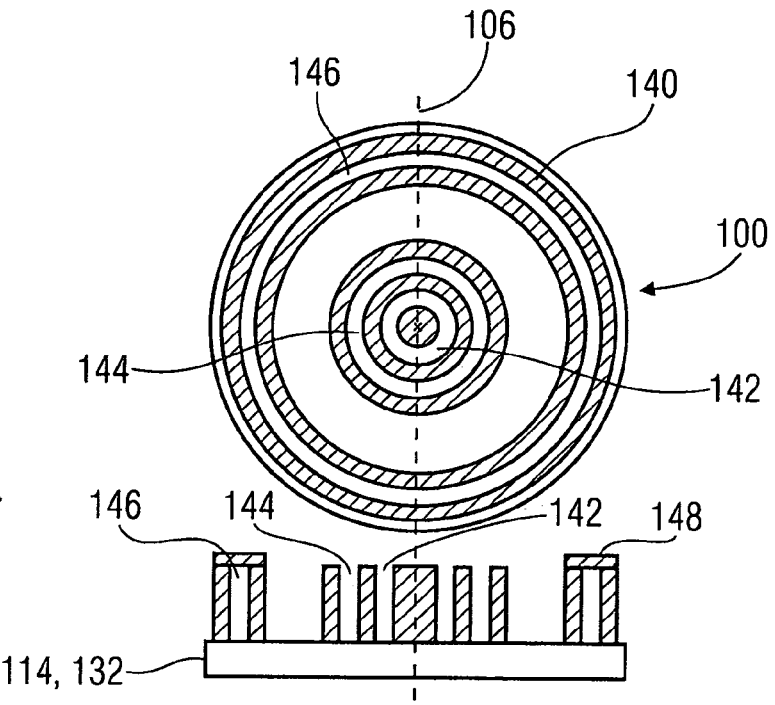
FIG. 8a
FIG. 8b
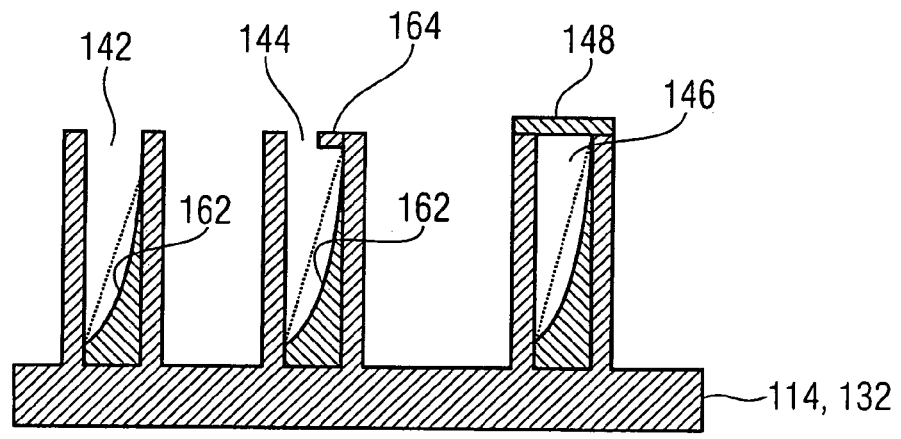
FIG. 9

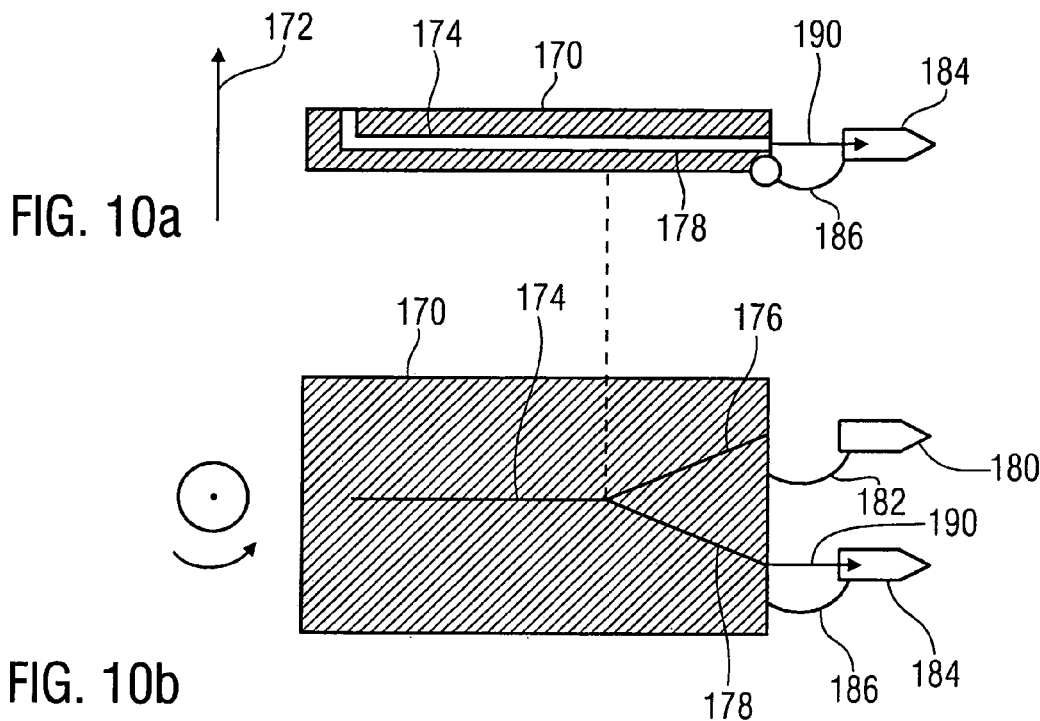
FIG. 10a
FIG. 10b
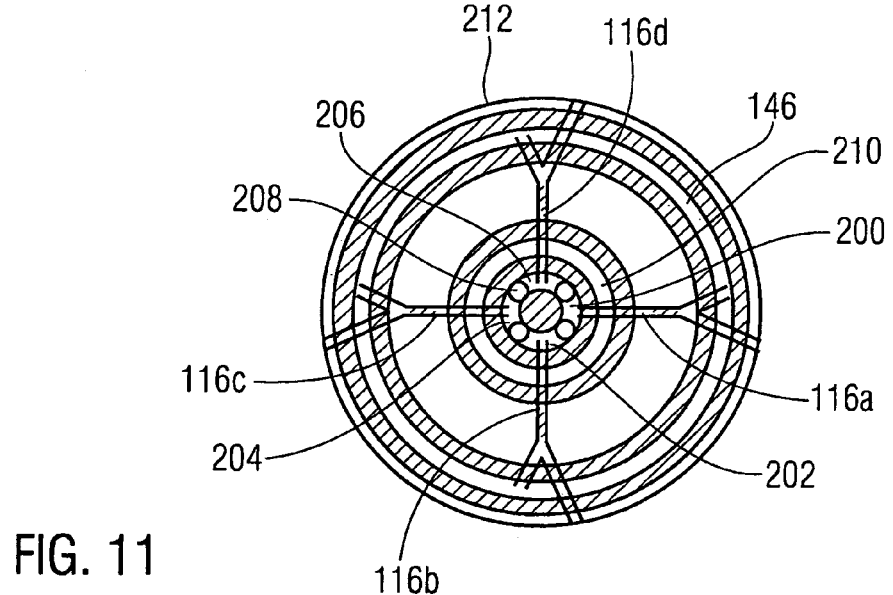
FIG. 11

LIQUID-HANDLING APPARATUS HAVING A LIQUID SWITCH AND METHOD FOR HANDLING LIQUIDS

BACKGROUND OF THE INVENTION

1. Field of the Invention

The present invention relates to the field of fluidics and, in particular, a liquid-handling apparatus having a liquid switch and a method for handling liquids. More particular, the present invention relates to a liquid-handling apparatus and method in which liquid volumes are driven by the centrifugal force and in which liquid volumes can be routed from a common inlet to one of two outlet channels, into which the inlet channel branches.

2. Description of Prior Art

Rotating disks have been introduced as convenient platforms, which allow flow control based on centrifugal forces, see M. J. Madou and G. J. Kellogg: "LabCD: A centrifuge-based, microfluidic platform for diagnostics", in Proceedings of SPIE, vol. 3259, 1998, pp 80-93; Michael J. Felton, "CD-based fluidics may offer a simple pumping alternative for lab-on-a-chip systems for some everyday applications", Analytical Chemistry, Vol. 75, No. 13, Jul. 1, 2003, pp. 302A to 306A; G. Ekstrand et al., "Microfluidics on a rotating CD", Proceedings of µTAS 2000, Eds. A. van den Berg, W. Olthuis and P. Bergveld; C. T. Schembri et al., "Centrifugation and capillarity integrated into a multiple analyte whole-blood analyzer", vol. 17, no. 3, ppl 99 to 104, 1995; and D. C. Duffy et al., "Rapid prototyping of microfluidic switches in poly (dimethyl siloxane) and their actuation by electro-osmotic flow", J. Micromech. Microeng. 9, pp. 211 to 217, 1999.

Centrifugals systems are known from the following companies: Abaxis at www.abaxis.com; Gyros at www.gyros.com; Tecon at www.tecan.com.

The centrifugal force creates an artificial gravity pointing in a radial direction. Flow control on rotating platforms is, for instance, achieved by capillary-burst valves, which are hydrophobic patches blocking a flow until a specific angular speed is reached. So far, the impact of the pseudo Coriolis force has not been considered for those platforms, despite the fact that the Coriolis force can prevail over all other forces beyond a certain speed of rotation.

Making use of the above-mentioned effect to realize a novel flow switch, which is controlled by the Coriolis force, is shown in the article T. Brenner, T. Glatzel, R. Zengerle, J. Ducrée: A Flow Switch Based on Coriolis Force, Proc. µTAS 2003, Oct. 5-9, 2003, Squaw Valley, Calif., USA, 2003, 903-906. The technique described in this article goes back to the inventors of the present invention and was made public on Oct. 5, 2004 for the first time. This article shows a flow switch, which is controlled by the Coriolis force on a centrifugal "lab-on-a-disk" platform (lab=laboratory). The Coriolis switch consists of an inverse Y-structure with one common upstream channel and two symmetric outlets. Above a certain threshold frequency $\omega_0$, the Coriolis force becomes dominant to direct nearly 100% of the flow in one of the outlets, which is selected by the direction of rotation. According to this article, the threshold frequency has been measured to be 350 rad s$^{-1}$ for a channel width of 360 micrometers and a depth of 125 micrometers.

Coriolis-induced switching has been published by the inventors in further publications, see Thilo Brenner, Thomas Glatzel, Roland Zengerle and Jens Ducrée: "Frequency Dependent Transversal Flow Control in Centrifugal Microfluidics", accepted for publication in Lab on a Chip, 2004; J. Ducrée, T. Glatzel, T. Brenner, R. Zengerle: "Coriolis-Induced Flow Control for Micro- and Nanofluidic Lab-on-a-disk Technologies", International Forum on Micro & Nano Integration (MINIT), 3-4. December 2003, Potsdam, Germany, 2003, pp. 147-153; J. Ducrée, T. Glatzel, T. Brenner, R. Zengerle: "Coriolis-Induced Flow Control in Centrifugal Microfluidics", Proc. NanoTech 2003; Nov. 25-27, 2003, Montreux, Switzerland, 2003; and J. Ducrée, T. Brenner, T. Glatzel, R. Zengerle: "Coriolis-Induced Switching and Mixing of Laminar Flows in Rotating Microchannels", Proc. Micro. Tec 2003, Oct. 14-15, 2003, Munich, Germany, 2003, 397-404.

With respect to the technique of a flow switch based on Coriolis force, the teachings of the above-mentioned publications going back to the inventors of the present invention are introduced herein by reference.

In the field of microbiology, stationary phases are used for extraction, upgrading and purification of substances. Extraction, upgrading and purification of important substances, such as nucleic acids, typically requires a sequence of liquid volumes to be run through a stationary phase, which can be formed by silica particles, for example.

The sequence of liquid volumes comprises a sample buffer, a wash buffer and an elution buffer in this order. Depending on the present chemical conditions, pH, temperature or ionic strength of the solution, for example, the target molecules bind to the stationary phase in a specific manner and, thereafter, solve in purified and an upgraded manner in the elution buffer.

In conventional systems, the liquid volumes are driven through the stationary phase, making use of classical hydrodynamic pumps, the gravity or by centrifugation, so-called "spin columns". After each step except for the last step, the substances driven through the stationary phase have to be removed from the bottom of the receiving vessel, generally manually in order to provide, in the last step, the pure eluate including the extracted sample. In a routine operation, this method comprising a plurality of steps is very time-consuming, cumbersome and liable to faults, in particular, if a plurality of samples have to be treated.

SUMMARY OF THE INVENTION

It is the object of the present invention to provide an improved liquid-handling apparatus having a liquid switch and an improved method for handling liquids, which permit discharging liquid volumes in an easy manner.

According to a first aspect of the invention, this object is achieved by a liquid-handling apparatus having a liquid switch, the liquid switch comprising;

a rotation body rotatable around a rotation axis;

a first channel formed in the rotation body and branching into a second channel and a third channel formed in the rotation body, wherein the first, second and third channels are adapted for a centrifugal liquid flow therethrough upon rotation of the rotation body, and wherein the channels are adapted to rout a liquid volume from the first channel into one of the second channel and the third channel dependent on at least one selected from the group comprising a frequency of rotation, a sense of rotation and an acceleration of rotation of the rotation body.

According to a second aspect, the invention provides a method for handling liquid, comprising:

delivering a liquid volume to an inlet of a first channel branching into a second and a third channel, wherein the channels are formed in a rotation body and are adapted for a centrifugal fluid flow therethrough upon rotation of the rotation body, and routing a liquid volume from the first channel into one of the second channel and the third channel by rotating the rotation body while controlling at least one of the group comprising a frequency of rotation, a sense of rotation and an acceleration of rotation of the rotation body.

In embodiments of the invention, the first channel preferably symmetrically branches into the second channel and the third channel and wherein a controller is adapted to control a drive such that in a first phase, the rotation body is rotated in a first sense of rotation at a frequency of rotation above a given frequency to route a first liquid volume into the second channel; and in a second phase, the rotation body is rotated in a second sense of rotation at a frequency of rotation above the given frequency to route a second liquid volume into the third channel.

Above a critical frequency threshold, the outlet channel is merely chosen by the sense of rotation. In this embodiment, in order to build a binary fluidic switch for a sequence of liquid volumes, each of them to be directed to one particular outlet, the change of the sense of rotation preferably occurs during a time interval where the branch is dry. This can, in the preferred type of system, by implemented by a time-programmable dispenser delivering a sequence of liquid volumes to the channel inlets, preferentially in a contact-free fashion. The frequency of rotation is kept constant or at least kept above the threshold frequency, as long as liquid flow is present within the branch. Dispensing is interrupted during the finite time interval required for changing the sense of rotation, i.e. when the (absolute value of) transitional frequency falls below the critical threshold, such that binary switching would not be guaranteed.

In other embodiments of the invention, the first channel branches into the second and third channels asymmetrically and wherein the controller is adapted to control the drive, such that, in a first phase, the rotation body is rotated in a first sense of rotation at a frequency below a given frequency to route a first liquid volume into the second channel, and, in a second phase, the rotation body is rotated in the first sense of rotation at a frequency above the given frequency to route a second liquid volume into the third channel. Note that also the asymmetric channel structure can, in principle, be switched by changing the sense of rotation.

The channel structure of the inventive liquid switch comprises an inlet channel and two outlet channels branching in different directions from the inlet channel.

The respective given frequency is such that at rotation at a frequency above the given frequency, the Coriolis force and/or centrifugal acceleration prevails and substantially the whole liquid volume is routed or switched into the designated channel under the influence of the Coriolis force and/or centrifugal acceleration.

Thus, the present invention is based on the recognition that a liquid switch can be implemented utilizing the Coriolis force and or the Euler force, which represent inertial forces appearing in rotating systems.

Starting from this approach, it is a further goal of the present invention to provide a system and a method for permitting a substantially automated handling of liquids in liquid systems in which different liquid volumes are passed through the same channel and, after same have passed the channel, are available separate from each other.

In order to achieve this goal, according to a further aspect, the inventive liquid-handling apparatus comprises a dispensing unit, a drive for rotating the rotation body and a controller.

The dispensing unit comprises at least one, preferably contact-free and/or stationary (i.e. not rotating with the rotation body), dispenser for delivering liquid volumes to the rotation body. The controller is adapted to control the dispensing means and the drive such that a sequence of liquid volumes are passed through the first channel and routed to the second or third channel, such that liquid volumes are present at the branch between the first channel and the second and third channels only at a time at which the rotation body is rotated in a manner to make sure that the respective liquid volume is routed to the second or third channel in a defined manner.

Thus, according to this aspect, the present invention permits a substantially automated operation for passing different liquid volumes through the same channel and making the different liquid volumes available and separate from each other at a plurality of outputs. In this regard, the present invention is particularly suited for applications in which different liquid volumes, such as a sample buffer, a washing buffer and an elution buffer, have to be passed through a stationary phase and wherein the elution buffer must be available separate from the other liquid volumes.

The invention concerns a binary hydrodynamic switch for centrifugal flows through a rotating fluidic network. The core of the liquid switch (flow switch) consists of a preferably radial inlet channel, which branches into two outlet channels. An incoming flow can be completely diverted into one particular outlet by means of inertia, i.e. the Coriolis pseudo force and/or the centrifugal acceleration. For the preferred Coriolis force based mechanism, the outlet is selected, above a given absolute value of the threshold frequency, by the sense of rotation in case of a symmetrical branch, or by the frequency of rotation only in case of an asymmetrical branch.

In other words, according to preferred embodiments, the present invention provides a network of liquid conduits, which rotates about a central axis and which consists of an inlet near the center of rotation, a channel with components in a radial direction, followed by a binary branch into two outlet channels. A liquid volume can be driven by the centrifugal force from an inlet to one distinct outlet, which is addressed by the sense of rotation and/or the frequency of rotation and/or the rotation acceleration.

The channels of the inventive liquid-handling apparatus are adapted for a centrifugal liquid flow therethrough, since the respective inlets thereof are located at a radial inner position when compared to the position of a respective outlet of the channels. Thus, by rotating the rotation body, a liquid flow is effected from the respective inlet to the respective outlet.

In preferred embodiments of the present invention, a sequence of liquid volumes, which should preferably be separated in time, can be introduced into the structure and each volume can individually be directed to a distinct outlet selected by the sense of rotation, the frequency of rotation and/or the rotational acceleration. The inventive liquid-handling apparatus can comprise a preferably contact-free dispenser. The contact-free dispenser is preferably able to deliver liquid volumes at a time-programmable flow rate, e.g. a rectangular ramp oscillating between constant flow rates and interrupted flow, to the inlet of the first channel.

In preferred embodiments of the invention, the supply of the liquids occurs via reservoirs, which are fluidically and mechanically connected to the inlet of the first channel. Moreover, in preferred environments, reservoirs are mechanically attached to inlets and/or outlets of the channel network, thus resting in the frame of reference rotating with the rotation body. In this regard, the rotation body may comprise a disk in which the channel structures are formed and a top part attached to the disk in which the reservoirs are formed. The reservoirs are preferably balanced, e.g. annular or point-symmetric with respect to the rotating motion, i.e. with respect to the axis of rotation of the rotation body.

The rotating reservoirs are either prefilled, releasing their liquid load, for instance, at a given time or trigger signal or, in the preferred system, they are made fluidically accessible, e.g. via an annular, slit-like opening on their top, for the contact-free dispenser resting in the lab frame. These open-end rotating reservoirs can, in principle, be continuously provided with liquid flows, i.e. their operation is not restricted to dispensing of droplets, which has to be synchronized to the rotating motion of the localized channel inlets. The rotating reservoirs should be protected against centrifugal overflow and they should be balanced, e.g. exhibiting a cylindrical symmetry, to mechanically equilibrate the system.

One of more of such rotating reservoirs can also be mechanically and fluidically attached to one or more channel outlets to collect to the processed liquids. The outlet reservoirs can be protected, e.g. by a full encapsulation, except for its inlet, against centrifugal overflow. Alternatively, one or more channels may have their outer ends open to the environment, thus ejecting, above a certain centrifugal force at the outlet, the processed liquid in a centrifugally driven free jet from the disk. Such an outlet can, for example, by provided with a centrifugal valve. These jets can be collected in vessels, e.g. reaction tubes, which are reversibly or irreversibly attached to the disk and which assume the proper orientation, ideally orienting according to the sum vector of the centrifugal force and the force of gravity which is perpendicular to the liquid surface, during rotation ("horizontal") and rest ("vertical") to contain the liquid during the entire frequency protocol.

The channel network may be provided in a flat disk, which is attached to the axis of a rotating engine forming the drive means and resting in the lab frame, which controls frequency of rotation.

According to embodiments of the invention, liquids are stored in inlet reservoirs before the network is set into rotation. In embodiments of the invention, rotating inlet reservoirs are fluidically accessible for a dispenser resting in the lab frame (stationary with respect to the rotation of the rotation body) and delivering liquid volumes, preferably in a contact-free fashion. A centrifugal overflow of the fluidically accessible inlet reservoirs can be avoided, at least up to a defined frequency of rotation, by a partially covered opening, a radially inclined cross-sectional contour line and/or a sufficiently high extension in the direction of the axis of rotation. Preferably, the rotating inlet reservoirs have an annular opening, through which same are accessible, such that a given liquid volume can be dispensed in a continuous flow during an arbitrary time interval into the rotating reservoir and the dispensing does not have to be synchronized with the azimuthal position of the disk during rotation or at rest. In order to avoid centrifugal overflow, the flowrate of the dispenser may be restricted to not exceed a critical limit of the liquid volume transiently stored in the rotating reservoirs.

In preferred embodiments, outlets of the rotating channels are provided such that a liquid jet of a processed liquid exits the one or more outlets in a free jet. In such embodiments, the flow from one or more outlets can be directed by a free jet ejection into a reservoir, e.g. a standard reaction tube, which is reversibly or irreversibly attached and thus rotating with the channel structure. By an additional bearing, the liquid surface can be aligned preferentially perpendicular to the resulting force of the centrifugal force and gravity.

Further embodiments of the present invention permit a parallization in that channel structures possessing preferably radial components and their interfaces, as well as connected structures, are distributed in an azimuthal direction, such that all structures can be spun simultaneously by the drive unit, i.e. the same vector of rotation and rotational acceleration. The several channel structures can be preferably formed or attached to a common substrate, preferably a planar disk. In such embodiments, one or a plurality of channel inlets are fluidically connected to reservoirs, which are fluidically insulated from other channel inlets in a network of parallel channels, such that the parallel channels permit simultaneously processing a plurality of different liquids, making use of the fluidically insulated reservoirs. In this regard, the plurality of fluidically insulated reservoirs can be formed by respective arc segments arranged in an annular manner and rotationally symmetrically with respect to the rotation axis, such that a volume allocation with respect to the respective reservoirs is obtained by the arc length of the respective segments.

Thus, several of such hydrodynamic switch structures can be arranged in parallel according to the cylindrical symmetry on the same (disk) substrate and, thus, be filled and switched simultaneously on the same drive unit. If the types or volumes of the liquids to each parallel channel are different, the inlet can be split into fluidically insulated reservoir compartments, e.g. annular segments, each of them fluidically connected to one or a subset of channel inlets. If these are the first liquids to be processed in a sequence of liquids, they can be prefilled before the common substrate is set into rotation. During spinning, liquids that are to be evenly distributed among the inlets can be continuously dispensed to a common cylindrically symmetric inlet reservoir possessing an annular slit opening. During rotation, a continuously dispensed liquid volume can be allocated according to the arc lengths of the segment. By an uneven distribution of the arc lengths, i.e. the time span, the dispenser is located above the reservoir compartments, different volumes can be delivered to the compartments during continuous dispensing. Also, the outlet reservoir can be divided into compartments, or a plurality of insulated outlet compartments can be provided, each of them fluidically connected to one or a subset of channel outlets and fluidically insulated from the other compartments.

In preferred embodiments, the inventive liquid-handling apparatus exhibits a modular set-up consisting of a drive unit module and a rotating module, comprising, e.g. a planar disk, which are reversibly attached to each other. The rotating module includes the channels and the reservoirs. Similar to a popular CD technology, the rotating module, possibly a disposable polymer cartridge, can easily be replaced with a reversible mechanical latch on the top of the axis of rotation.

According to a further general aspect of the invention, the inventive liquid-handling apparatus is provided or equipped with a stationary phase in the first channel (i.e. the inlet channel) of the liquid switch to run different analytical or preparative "chromatographic" protocols, such as chemical filtrations and extractions, which require a sequence of liquid volumes to be run through the same stationary phase and then to be collected in different receiving vessels. The stationary phase may, for instance, be a membrane or an agglomeration of particles held back by a frit or a geometrical structure and/or a surface coating.

Thus, in embodiments of the invention, a stationary phase is embedded in the channel prior to the binary branch. By the stationary phase, the inventive system is adapted to automate preparative and analytical protocols, e.g. nucleic acid extractions, filtrations or chromatographic separations at the stationary phase. The stationary phase may be represented by an embedded membrane, a geometrical structure, or particulates which are held back by step-flattening the downstream channel or a surface coating or a combination thereof.

Moreover, in embodiments of the invention, there is a plurality of branches, possibly possessing different geometries and, thus, different switching characteristics, in each fluidic channel network and the flow is directed at each branch according to the transient frequency of rotation and/or its change in time. In other words, a particular channel network may also include a network of switches, each of which can vary with respect to its geometry and position on the disk. At a given frequency of rotation, each switch may thus be in a different state, i.e. either selecting the leading or the trailing side of the structure, or below the critical frequency, distribute the flow among its two outlets. In a "Christmas tree" structure, exhibiting a multiply branch network, an initial volume introduced into the common route inlet can be distributed to the outlets according to switch geometries and the frequency of rotation.

SHORT DESCRIPTION OF THE DRAWINGS

Preferred embodiments of the present invention are explained hereinafter, making reference to the attached Figs. Throughout the Figures, the same elements are provided with the same reference numbers.

FIGS. 3a, 3b, 4a and 4b show schematic views of branched channels suited for the present invention;

Figure 7:
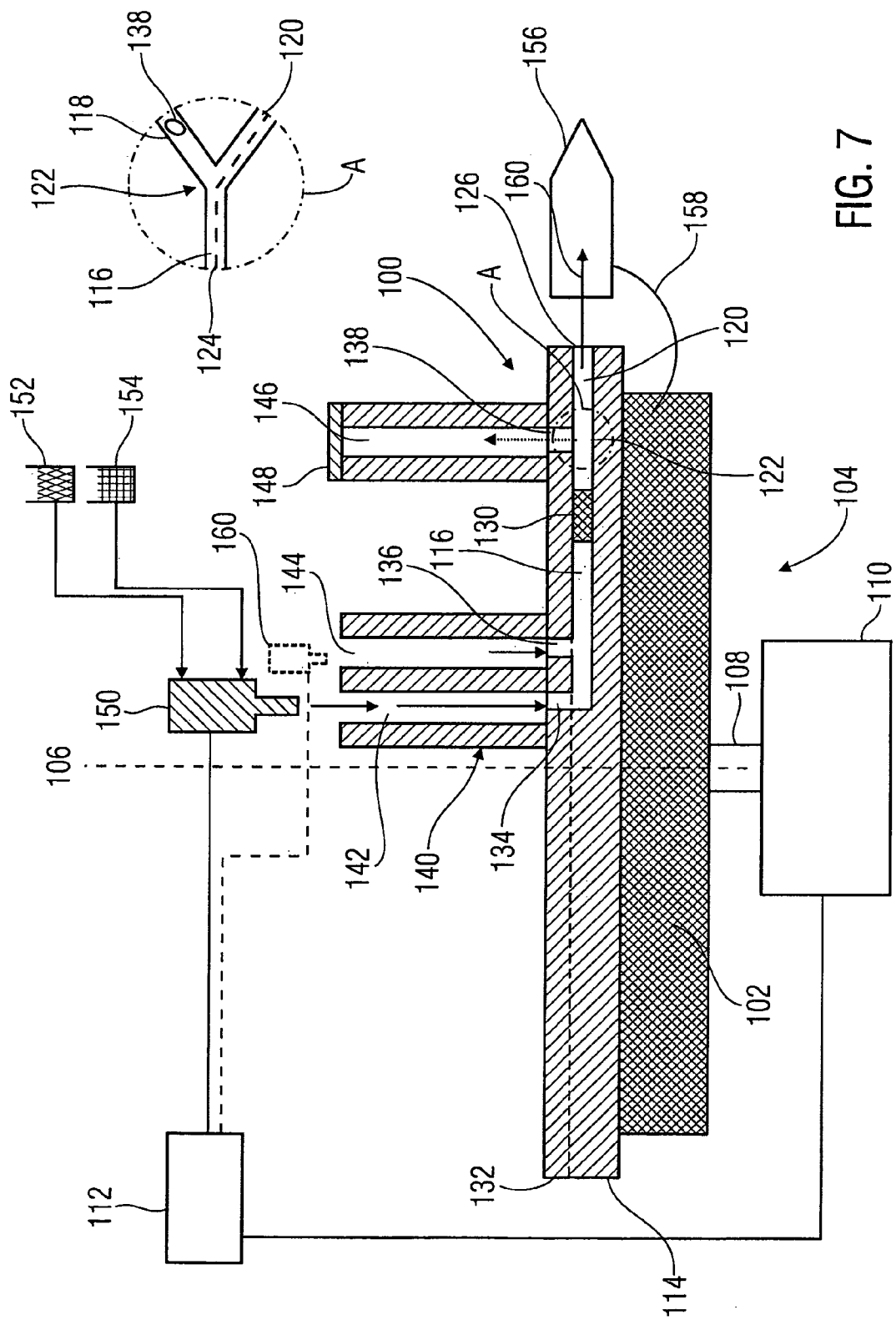
FIG. 7 is a schematic view of an embodiment of a liquid-handling apparatus according to the invention.
Figure 12:
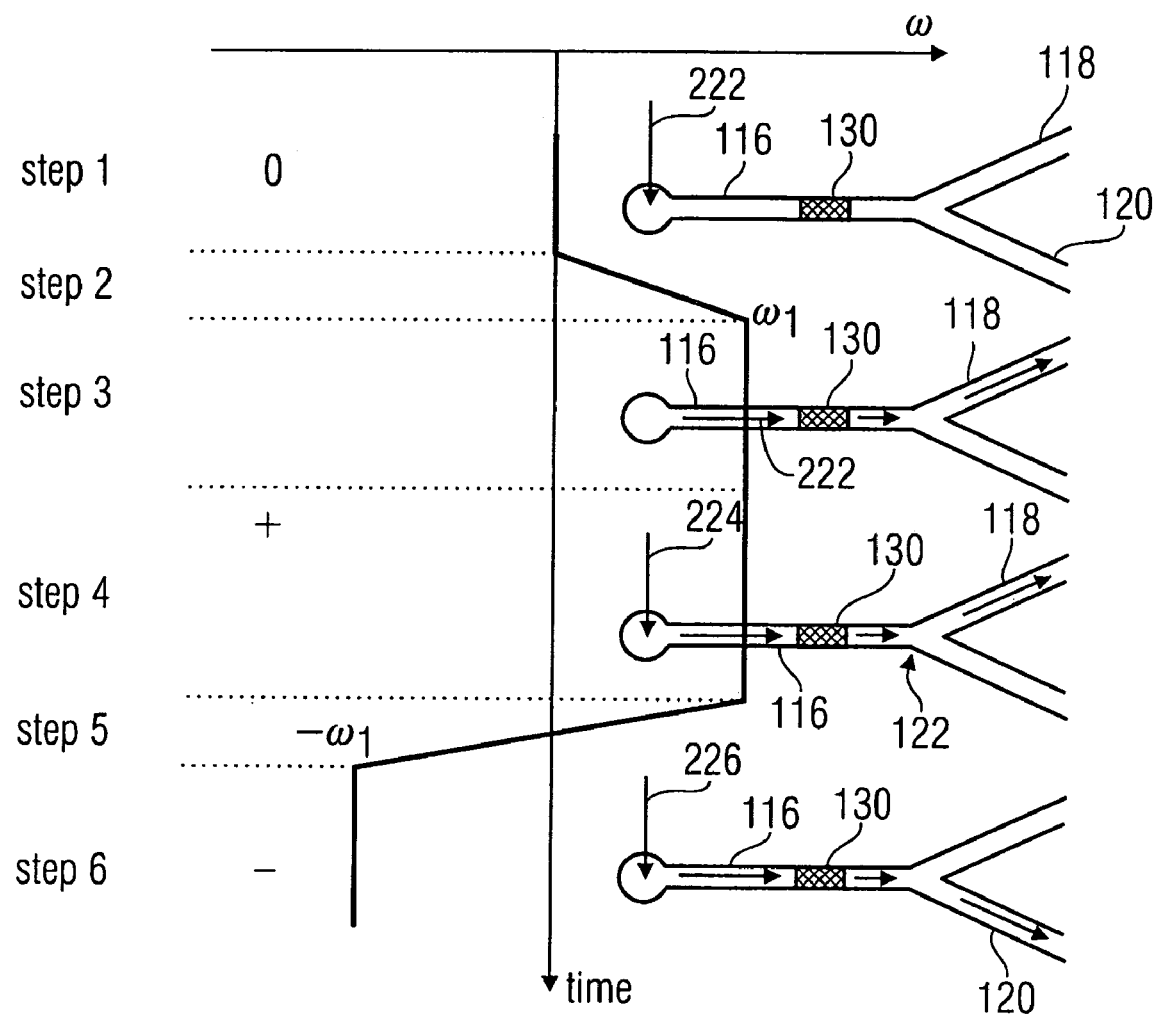
Figure 13:
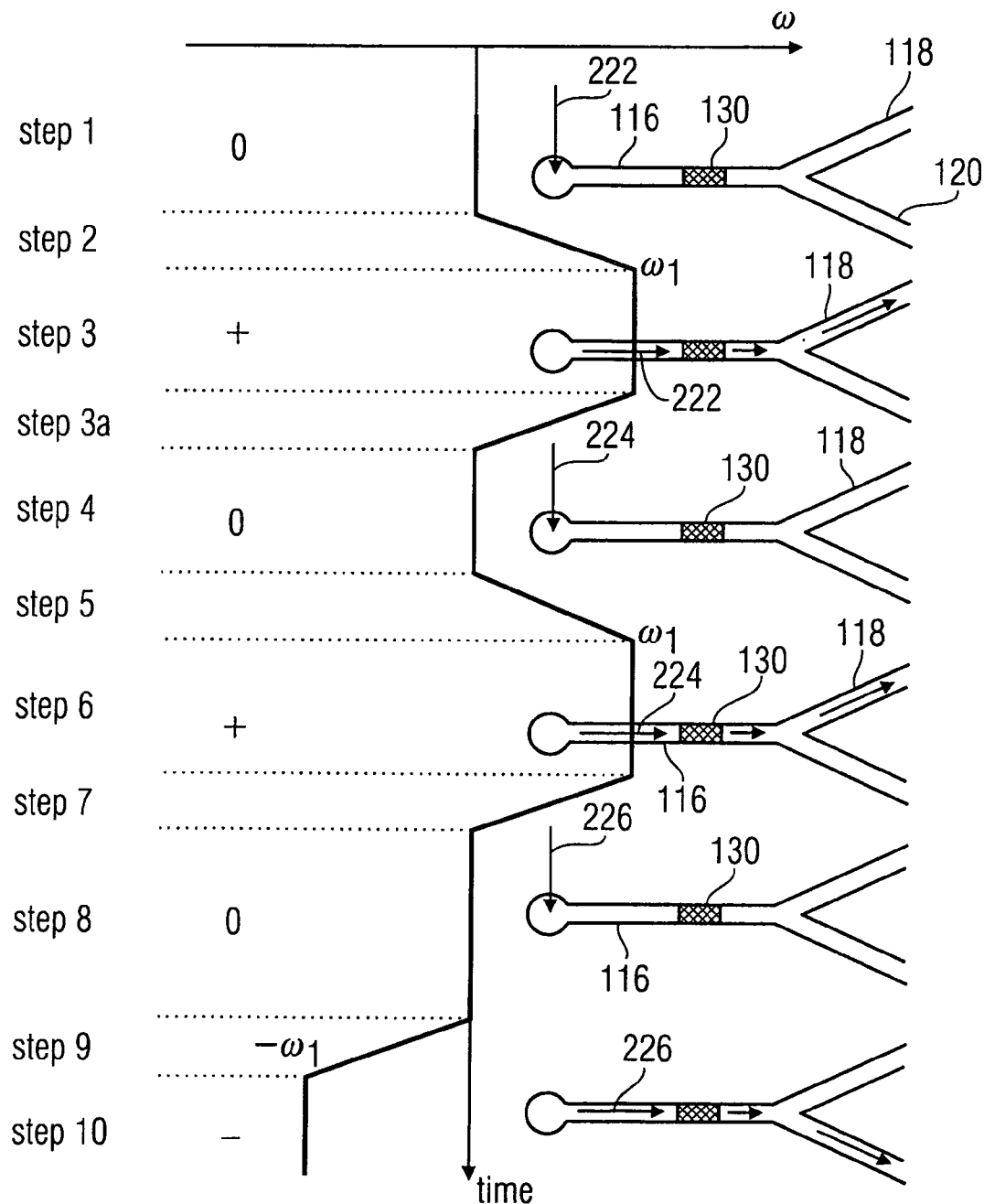
Figure 14:
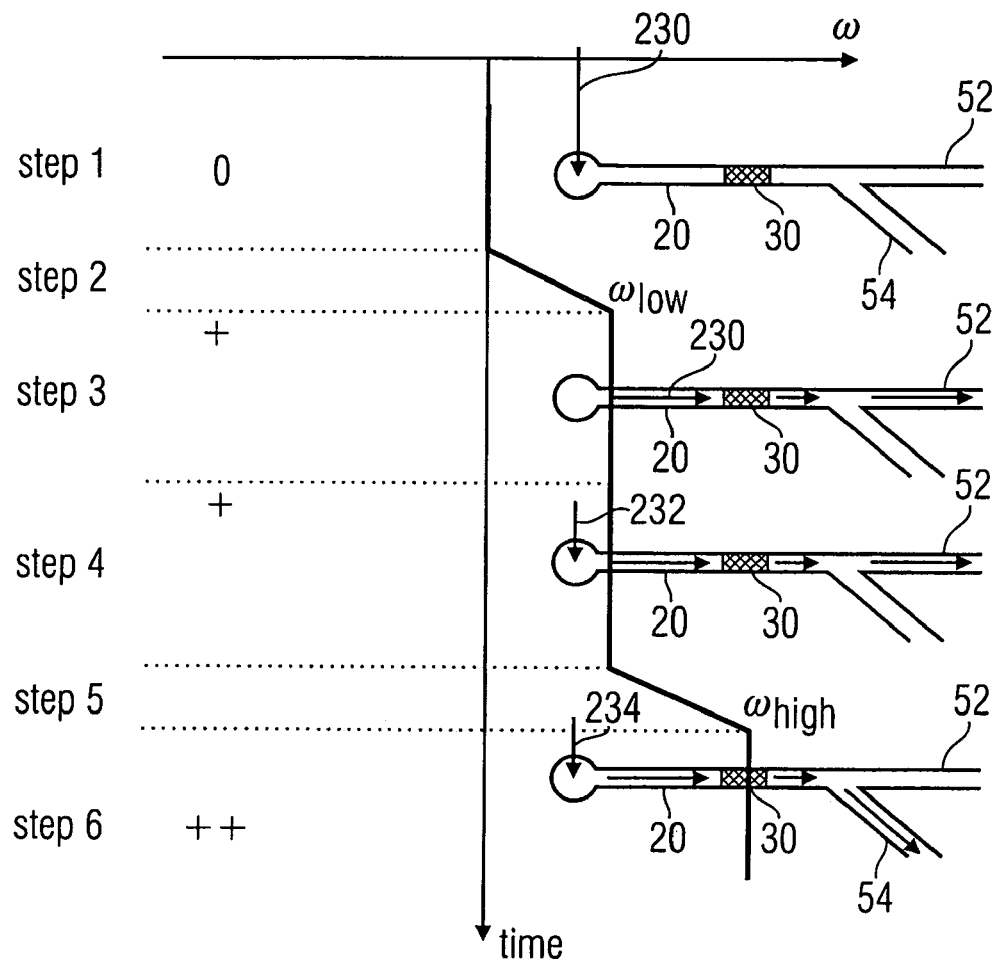

FIGS. 8a and 8b schematically show a top view and a cross-sectional view of the rotation body of the system shown in FIG. 7;

FIG. 9 shows a schematically cross-sectional view for illustrating overflow protection;

FIGS. 10a and 10b show schematic views for illustrating the arrangement of channels and outlet reservoirs in an embodiment of the invention;

FIG. 11 shows a schematic view for illustrating a rotation body having parallel channel structures;

FIGS. 12 to 14 show schematic views for illustrating embodiments of inventive methods for handling liquid volumes.

DESCRIPTION OF PREFERRED
EMBODIMENTS OF THE INVENTION

Figure 1:
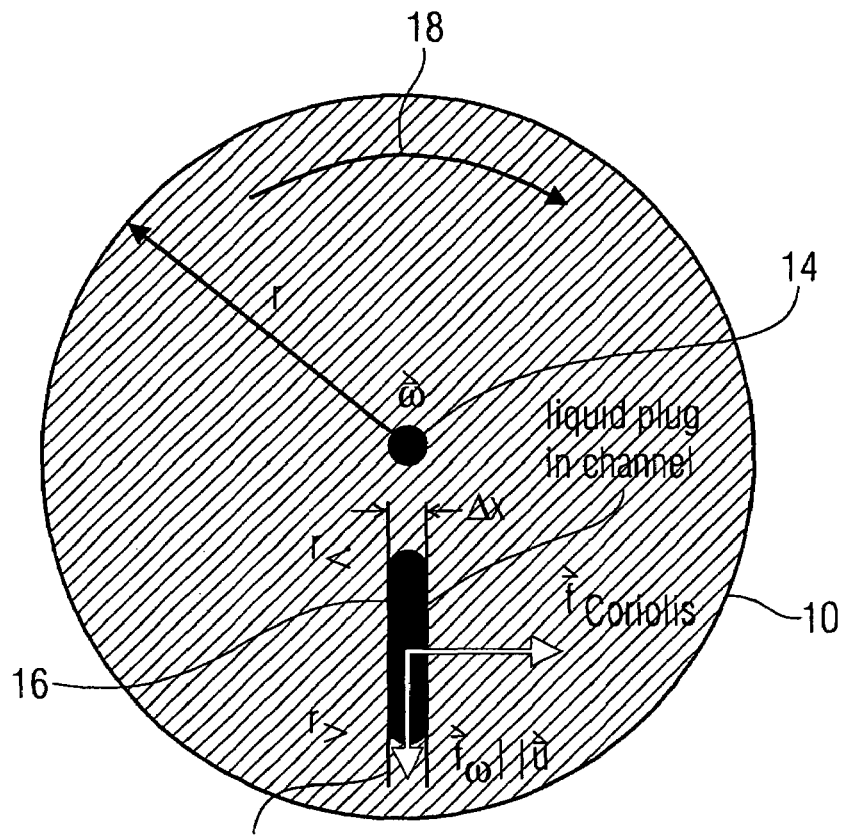
FIG. 1 shows a schematic representation for illustrating the Coriolis force.

The present invention relates to a liquid-handling system including a liquid switch based on the Coriolis force. FIG. 1 shows a rotating disk 10 in which a fluid channel 12 is formed. The fluid channel 12 extends in a radial direction with respect to an axis 14 of rotation. A liquid plug 16 in the channel 12 of the width $\Delta x$ on the disk 10 spinning at a angular velocity $\omega = 2\pi\nu$ is exposed to the radial centrifugal force $f_\omega$. $\nu$ denotes the frequency of rotation. The radial position of the plug 16 is characterized by its boundaries $r_<$ and $r_>$. With the sense of rotation, as indicated by the arrow 18, a Coriolis force $f_{Coriolis}$, appearing solely on the rotating, non-inertial frame of reference, acts perpendicular to the flow velocity u, wherein the flow velocity u is caused by the centrifugal force $f_\omega$ and is parallel thereto (for a channel extending in the radial direction).

The hydrodynamics on rotating disks is described by the Navier-Stokes equation. The centrifugal force density $$\vec{f}_\omega = -\rho \cdot \vec{\omega} \cdot (\vec{\omega} \times \vec{r})$$

is experienced by a liquid plug of mass density $\rho$ within a channel in radial r-direction on a disk spinning at $\omega$ $\omega = 2\pi\nu$ (FIG. 1) The balance of centrifugal and viscous forces can be expressed by $$-\rho \cdot \vec{\omega} \cdot (\vec{\omega} \times \vec{r}) = \eta \cdot \nabla^2 u$$

with u denoting the flow velocity and $\eta$ denoting the viscosity of the liquid.

In order to allow a simple analytical treatment, a 2-dimensional flow through a gap of width $$\Delta x = 2 \cdot x_0$$

instead of the rectangular channels in typical experiments is assumed. Setting the flow velocity u to zero at both channel walls, $u(-x_0) = u(x_0) = 0$, a parabolic flow profile is derived with the maximum velocity $$u_{max} = \frac{\rho \cdot \omega^2 \cdot \vec{r}}{2 \cdot \eta} \cdot x_0^2$$

in the center of the gap. The mean radial position of the liquid is expressed by $$\vec{r} = \frac{1}{2} \cdot (r_> + r_<)$$

with the inner and outer spacings of the liquid plug from the center of rotation denoted by $r_<$ and $r_>$.

When the resulting flow at a speed u is observed from a non-inertial frame rotating at $\omega$, i.e. with the disk at rest, an additional Coriolis force component $$\vec{f}_{Coriolis} = -2 \cdot \rho \cdot \vec{\omega} \times \vec{u}$$

appears. This pseudo-force acts perpendicular to the plane spanned by the flow velocity u and the angular frequency of rotation $\omega$. The ratio $$\frac{|\vec{f}_{Coriolis}|}{|\vec{f}_\omega|} = \frac{\rho \cdot \Delta x^2 \cdot \omega}{4 \cdot \eta}$$

compares the centrifugal force in radial direction to the transversal Coriolis force acting perpendicular to the direction of flow. Here the steady state at a constant frequency $d\omega/dt = 0$ without any rotational Euler acceleration $d\omega/dt$ is considered. For the liquid characteristics of water and a typical channel width $\Delta x = 200$ μm, the ratio roughly amounts to $10^{-2}\omega$. This way, for frequencies beyond only $\omega_0 = 100$ rad s$^{-1}$ (about 16 Hz), the Coriolis force even prevails the centrifugal force. The critical frequency $\omega_c$ for binary switching is typically larger than $\omega_0$.

Figures 2A, 2B:
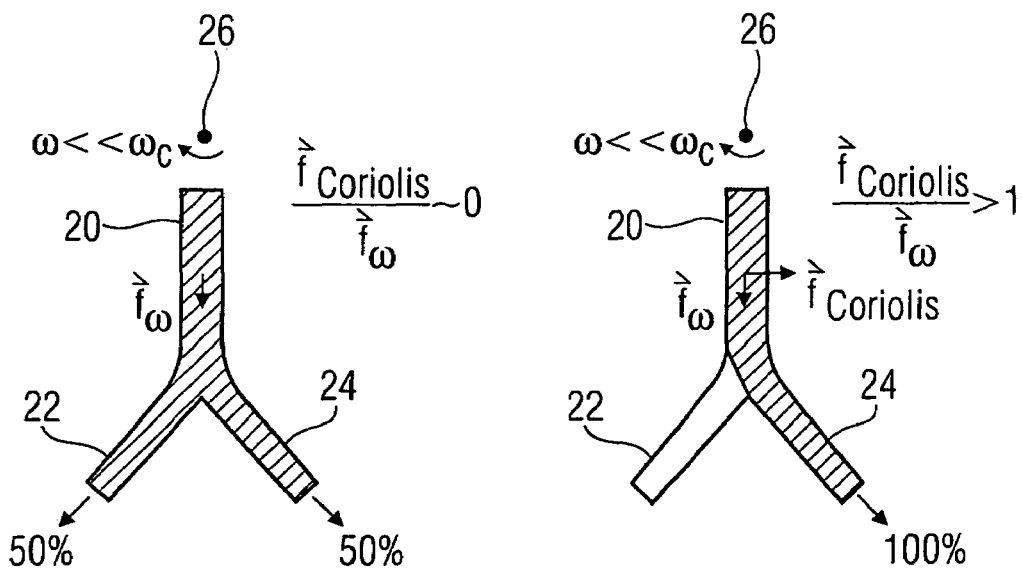
FIGS. 2a and 2b show a schematic view of a branched channel rotated at different frequencies.

FIGS. 2a and 2b show the channel structures of a fluidic switch according to an embodiment of the invention. The channel structure comprises an inlet channel 20, which branches into a first outlet channel 22 and a second outlet channel 24. The channel structure is rotatable around a rotation axis 26. In FIG. 2a, a situation is shown in which the rotation frequency is low when compared to the frequency $\omega_c$. At low frequency $\omega$, where the Coriolis force $f_{Coriolis}$ is negligible, the flow is divided up at same flow rates through both outlets 22 and 24. At frequencies beyond $\omega_c$, the Coriolis force dominates and diverts, aided by interfacial effects, 100% of the flow into one addressable outlet according to the direction of rotation. For the clockwise rotation shown in FIG. 2b, this is the outlet channel 24.

The switching effect for a symmetric channel structure, which depends on the frequency of rotation and the sense of rotation, is shown in FIGS. 3a and 3b. In FIGS. 3a and 3b, the inlet channel 20 and the outlet channels 22 and 24 are shown, wherein FIG. 3a shows a counter-clockwise rotation 32, while FIG. 3b shows a clockwise rotation 34. Rotation in both directions cause a centrifugal force $f_\omega$ and a resulting liquid flow 36 in the inlet channel 20.

The counter-clockwise rotation 32 at a frequency above the critical frequency threshold $\omega_c$ causes a Coriolis force $f_{Coriolis}$ indicated by the arrow 38, such that the flow 36 is fully routed into the second outlet channel 24 as flow 40. The clockwise rotation 34 at a frequency above the critical frequency threshold $\omega_c$ according to FIG. 3b causes a Coriolis force in the direction of the arrow 42 in FIG. 3b and routes the flow 36 fully into the first outlet channel as flow 44.

An embodiment of a liquid switch comprising an asymmetric branch is shown in FIGS. 4a and 4b. As shown in FIGS. 4a and 4b, an inlet channel 20 branches into a first outlet channel 52 and a second outlet channel 54. The branch is asymmetrical in that the first outlet channel 52 extends in the same (or substantially the same) direction as the inlet channel 20, while an angle is provided between the second outlet channel 54 and the inlet channel 20. The angle is in an opposite direction when compared to the sense of rotation 32.

In the situation shown in FIG. 4a, the channel structure is rotated at a first low frequency $\omega_1$, resulting in a very small Coriolis force 56. Thus, due to inertia, the flow 36 in the inlet channel caused by the centrifugal force $f_\omega$ follows the radial channel axis and is routed into the first outlet channel 52, flow 58. Above a critical frequency threshold and the indicated counter-clockwise sense of rotation 32, the caused Coriolis force 60 prevails to route the flow 36 into the inclined outlet channel 54, flow 62. Thus, for the proper sense of rotation, for low frequencies below the given critical frequency threshold, the flow is routed into the first outlet channel 52, while for frequencies above the critical frequency threshold, the flow is routed into the inclined outlet channel.

The radially directed centrifugal force changes with $\omega^2$ and, therefore, the flow velocity u changes with $\omega^2$. Thus, the ratio between the transversal Coriolis switching force and the centrifugal force is proportional to the frequency of rotation $\omega$. At low frequencies of rotation, the centrifugal force predominates, so that a deflection caused by the Coriolis force can be neglected. Above a given frequency $\omega_0$, the transversal Coriolis force predominates over the centrifugal force. The critical switching frequency $\omega_c > \omega_0$ depends on the geometry of the channel structure, interfacial tensions and the viscosity of the liquid. Thus, at a respective branch, the flow is routed to a defined outlet depending on the frequency of rotation $\omega$ or the acceleration of rotation $d\omega/dt$. The frequency threshold for a given liquid and a given geometry of the channel structure necessary for obtaining a substantially full switching between two outlet channels can be derived by simulating the flow rates through the respective channel structures.

Figure 5:
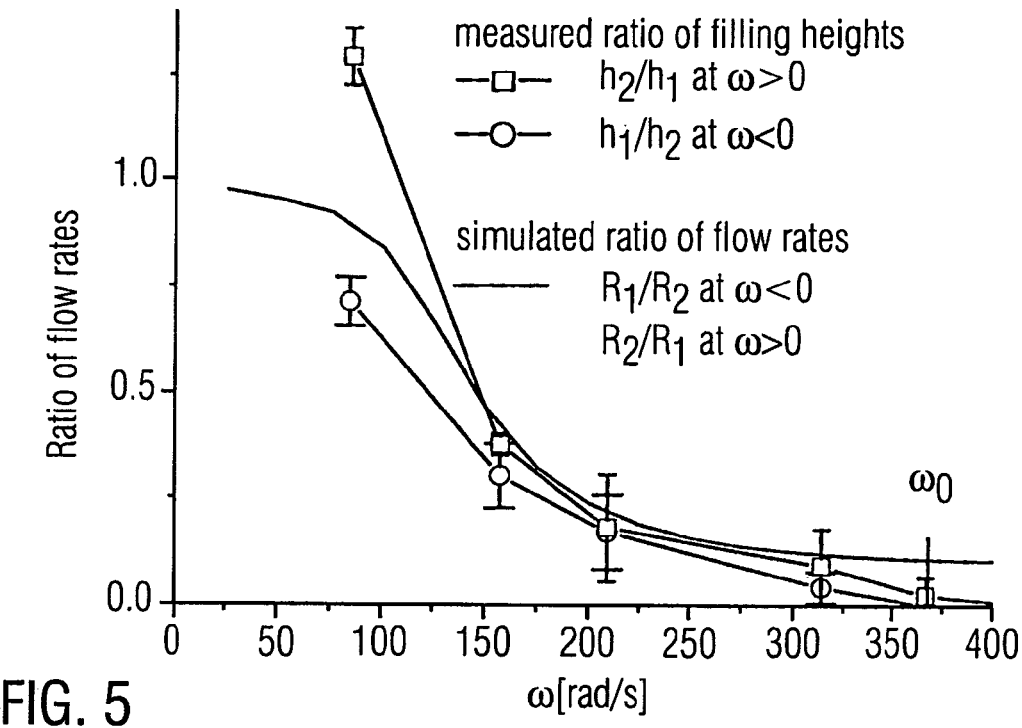
FIG. 5 shows a comparison of measured results and simulated results with respect to the ratio of flow rates versus the rotation frequency.

A comparison between measured results and simulated results neglecting interfacial effects for a structure as shown in FIGS. 3a and 3b is shown in FIG. 5. The results shown in FIG. 5 were obtained for a channel width of 360 micrometers and a depth of 125 micrometers. The measured flow rate into each outlet is obtained by collecting the volumes issued from the outlets into designated receiving vessels $R_1$ and $R_2$ over a time span T. For a known geometry (cross-sectional surface) of the reservoirs $R_1$ and $R_2$, the volumes V1 and V2 are calculated from the filling heights $h_1$ and $h_2$ and the (mean) flow rates can then be calculated by $V_1/T$.

The ratios of measured filling heights $h_1$ and $h_2$ in the receiving vessels $R_1$ and $R_2$ and simulated flow rates at the outputs over the frequency of rotation $\omega$ in both rotational directions represented by $\omega>0$ (counter-clockwise) and $\omega<0$ (clockwise) are shown. The ratio of flow rates at frequencies below 75 rads$^{-1}$ (approximately 12 Hz) shifts from 1.0 to nearly 0 towards higher frequencies due to an increasing Coriolis force. Beyond 350 rads$^{-1}$ (about 55.7 Hz), the ratio amounts to 0, since the entire flow is diverted into one outlet.

Asymmetries in the experimentally observed rates are attributed to geometrical deviations of the outlet channel. Moreover, the simulation does not take into account the free liquid-gas interface in the branch region, so that same represents an approximation of the experimental situation. This explains that even for the highest frequencies, no full diversion of the flow is observed in the simulated results. However, especially for intermediate frequencies, the diversion of flow is well reproduced by the simulation.

Figure 6:
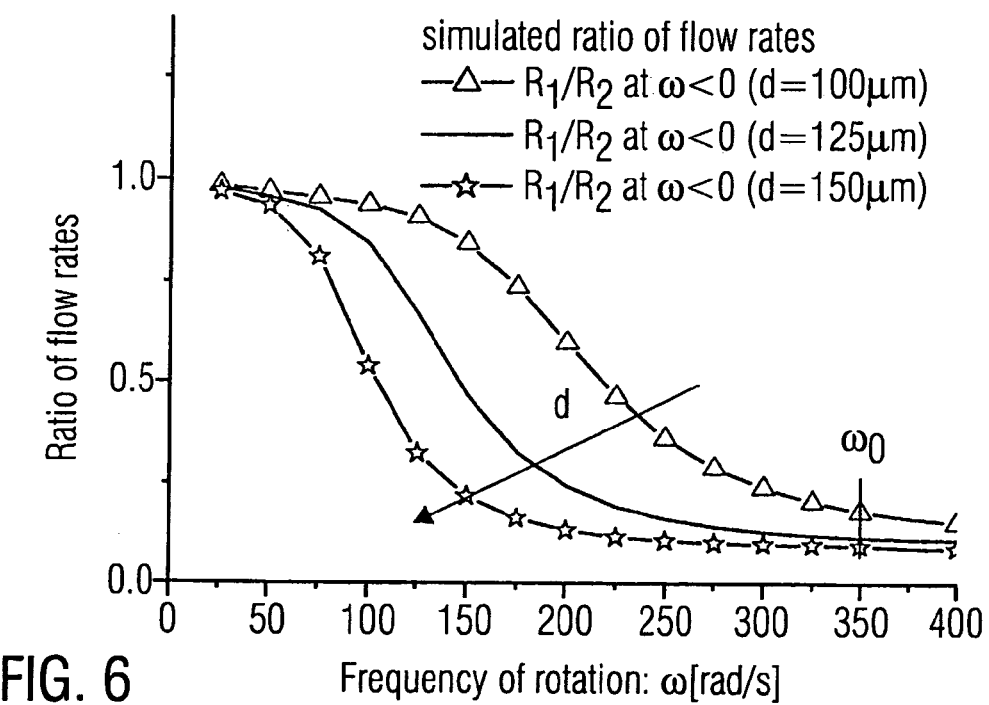
FIG. 6 shows graphs representing simulated ratios of flow rates depending on the channel depth.

FIG. 6 shows simulated flow rate ratios as a function of the spinning frequency $\omega$ with the channel depth d as a parameter. As the channel depth d increases, flow velocities increase due to the lower hydrodynamic resistance to enhance the impact of the transversal Coriolis force. Hence, towards increasing d, the slope of the switching curve in the transitional regime becomes steeper and the overall switching frequency, i.e. the threshold frequency, drops.

A preferred embodiment of the present invention, in which a hydrodynamic switch as explained above is implemented to integrate, automate and possibly parallelize the common extraction protocol of nucleic acids by means of a stationary phase embedded into a disk substrate and a sequence of liquids, a sample solution, a wash buffer and an elution buffer, is explained.

The corresponding device set up is illustrated in FIG. 7. The system comprises a rotation body 100 attached to a support plate 102, which is part of a drive 104 for rotating the rotation body 100 around a rotation axis 106. For example, the rotation body can be attached to the support plate similar to conventional compact disks, making use of an axle 108, or the like. The axle 108 and the support plate 102 can be rotated by a rotation engine 110. The rotation engine 110 is controllable by a controller 112, so that the rotation body 100 can be subjected to an adjustable rotation.

The rotation body 100 comprises a disk 114 in which the channel structures of a hydrodynamic switch are provided. To be more specific, an inlet channel 116, a first outlet channel 118 and a second outlet channel 120 are formed in the rotation disk 114. A top view of the portion 122 at which the inlet channel 116 branches into the first and second outlet channels 118 and 120 is shown in the magnified section A. In addition, it is to be noted that the cross-sectional view shown in FIG. 7 is along the line 124 shown in the magnified section A.

The second outlet channel 120 has an outlet 126, which opens to the side of the rotation body 100. A stationary phase 130 is embedded into the inlet channel. The stationary phase may be a membrane or an assemble of particles held back by a frit or a geometrical structure and/or a surface coating in the inlet channel 116.

A cover 132 is provided on the top surface of the rotating disk 114. The cover 132 comprises a first inlet opening 134 and a second inlet opening 136. Moreover, the cover comprises an outlet opening 138. A reservoir structure is provided on top of the cover 132, which comprises a first reservoir 142, a second reservoir 144 and a third reservoir 146. The first reservoir 142 is fluidically connected to the first inlet opening 134, the second reservoir 144 is fluidically connected to the second inlet opening 136 and the third reservoir 146 is fluidically connected to the outlet opening 138. As can be seen from FIGS. 8a and 8b showing a simplified top view and a cross-sectional view of the rotation body 100, the reservoirs 142, 144, 146 are arranged concentrically with respect to the axis of rotation 106. For simplicity, the corresponding parts of the reservoir structures in the left-hand portion of FIG. 7 are omitted.

The third reservoir 146 is covered by a cap 148 at the top thereof. In order to show the structure of the reservoir 146, the cap is omitted in the top view of FIG. 8a.

In the embodiment shown in FIG. 7, the first reservoir 142 represents a reservoir for receiving a wash buffer and an elution buffer. The second reservoir 144 represents a sample reservoir. The third reservoir 146 represents a waste receiving vessel. In this regard, the outlet opening 138, to which the receiving vessel 146 is fluidically connected, is fluidically connected to the first outlet channel 118. The outlet opening 138 is constructed such that a liquid, which has passed therethrough into the receiving vessel 146, does not flow back into the first outlet channel 118 under operation conditions, i.e. by gravity, or the like.

A free jet dispenser 150 is provided and positioned with respect to the first reservoir 142, such that a wash buffer and an elution buffer can be dispensed into the first reservoir 142 in a contact-free manner. To this end, the dispenser 150 is attached in alignment with the top opening of the first reservoir 142, such that, if desired, it is possible to dispense liquid volumes into the first reservoir 142 during rotation of the rotation body. The dispenser 150 is further connected to the controller 112, wherein the delivery of liquid volumes by the dispenser 150 is controlled by the controller 112. Moreover, the dispenser 150 is fluidically connected to a wash buffer supply 152 and to an elution buffer supply 154.

In addition, a second dispenser 160 may be provided aligned with the top opening of the second reservoir 144 to deliver a sample buffer into the second reservoir 144. The dispenser 160 may also be connected to the controller 112 and is adapted to preferably provide the sample buffer into the reservoir 144 in a contact-free manner.

FIG. 7 further shows a receiving vessel 156, which is connected to the support plate 102 or to the rotation body 100 in a reversible manner by a corresponding mounting schematically shown at 158 in FIG. 7. The receiving vessel 156 and the mounting 158 are adapted to receive a free jet 160 ejected from the outlet opening 126 of the second outlet channel 120. The receiving vessel 156 is attached for rotation with the rotation body 100. The receiving vessel 156 can be a tube, which is reversibly attached to the outlet of the outlet channel 120, which is, as will be explained later, designed for a last elution step. In order to prevent the outflow of liquid, the axis of symmetry of the tube should ideally be perpendicular to the resulting vector of centrifugal and the gravitational force. This can be realized by an additional axis of rotation, e.g. a mechanical bearing, which lets the axis of the tube 156 align parallel to the vertical gravitational force at rest and align horizontally, parallel to the centrifugal force, for rotation at which the free jet 160 is ejected.

The drive 104 comprising the support plate 102, the axle 108 and the rotation engine 110 can be formed by a centrifuge, the rotation frequency and/or the sense of rotation of which are adjustable.

Typical volumes of liquids to be processed range on the order of up to several hundred microliters. They can, therefore, not be completely stored on flat disks, which are a common substrate used for centrifugal microfluidic systems. Such flat disks can typically store volumes up to a few micro liters only. Thus, in preferred embodiments of the present invention, as shown in FIG. 7, a fluidically and mechanically attached reservoir structure 140 comprising cylindrical reservoirs is provided, so that the storage capacity can be significantly extended.

In the preferred embodiment shown, the disk-based system exhibits three concentric, rotating reservoirs are provided, namely, on the inner side, a sample reservoir and a wash buffer and elution buffer reservoir, and, on the outer perimeter, a reservoir collecting the processed sample and the wash buffer after passing the stationary phase. Additionally, the reservoir structure could include a fourth reservoir, on the outer perimeter, for the typically much smaller volume of the elution buffer containing the extracted and purified DNA.

In the preferred embodiments of the invention, the elution buffer containing the extracted and purified DNA is output at the side face of the rotation body as a free jet 160, as shown in FIG. 7. It is clear that it is not necessary that the innermost reservoir represent the wash buffer and elution buffer reservoir. Alternatively, the first reservoir 142 could be provided as the sample reservoir, while the second reservoir 144 could be provided as the wash buffer and elution buffer reservoir. Moreover, separate reservoirs could be provided as wash buffer reservoir and as elution buffer reservoir. Also the outer channel opening may not need to be located in the side surface, but they can also be located on the top or bottom surface as long as a centrifugally propelled jet can still leave the disk.

FIG. 9 schematically shows a cross-sectional view of reservoirs, which are protected against centrifugal overflow. To this end, the outer waste reservoir 146 can, for example, be completely covered by the cap 148. The fluidically accessible reservoirs 142 and 144 feature high walls, such that the liquid surface 162 does not rise above their top, up to a given volume and a given frequency of rotation. Also the dispense rate must be restricted in a way that the liquid volume transiently stored in the rotating reservoirs does not exceed a certain limit Moreover, the reservoirs, which must be fluidically accessible to the contact-free dispenser resting in the lab frame, could be provided with an additional wall, which extends in the radial direction (as shown at 164 for the reservoir 144 in FIG. 9), in order to avoid overflow up to a given stored volume. The shown liquid surfaces 162 are obtained during rotation due to the centrifugal force $f_\omega$.

FIGS. 10a and 10b show a schematic cross-sectional view and a schematic top view of an alternative embodiment of a rotation body that can be used for the present invention. A rotation body is schematically shown at 170 and is rotatable about an axis of rotation 172. An inlet channel 174 branches into a first outlet channel 176 and a second outlet channel 178.

It is to be noted that the cross-sectional view of FIG. 10a is along the inlet channel 174 and the second outlet channel 178. A first receiving vessel 180 is attached by a mounting 182 to be aligned with the outlet of the first outlet channel 176. A second receiving vessel 184 is mounted by a mounting 186 to be aligned with the outlet opening of the second outlet channel 178. The mounting of the receiving vessels 180 and 184 can be similar to that of the receiving vessel 156 explained above. Upon rotation of the rotation body 170 in the counter-clockwise direction at a frequency above the critical frequency, a liquid volume driven through the inlet channel 174 is switched, i.e. routed, through the second outlet channel 178 and ejected into the receiving vessel 184, as indicated by the arrow 190 in FIGS. 10a and 10b. Upon rotation of the rotation body in the clockwise direction (not shown), the liquid volume is switched into the first outlet channel 176 and ejected into the first receiving vessel 180. Thus, according to FIGS. 10a and 10b, a centrifugally driven free jet ejection into receiving vessels, reaction tubes for example, which are attached to the rotating unit, is obtained.

An embodiment permitting a parallel processing of several samples is schematically shown in FIG. 11. To be more specific, FIG. 11 shows a schematic top view of a rotation body permitting a parallel processing. According to FIG. 11, four sample reservoirs 200, 202, 204 and 206 are provided by insulated respective segments of an annular structure, making use of respective insulators 208. Thus, the concentric sample inlet reservoir is split into four compartments 200 to 206, each of which being connected to an inlet channel 116a, 116b, 116c and 116d. Each of the inlet channels branches into a first and a second outlet channel, as explained above with respect to FIG. 7. Moreover, a stationary phase is embedded into each of the inlet channels.

In the embodiment shown in FIG. 11, a wash buffer and elution buffer reservoir 210 is fluidically connected to each of the inlet channels 116a to 116d. Thus, according to the embodiment shown in FIG. 11, four samples can be processed in parallel. The parallelization is obtained by a rotationally symmetrical replication of the channel structures, as well as the inlets and outlets. A respective receiving vessel can be associated to each of the outlet channel opening at the side face of the rotation body 212 shown in FIG. 11, as explained above with respect to the outlet channel opening 126, shown in FIG. 7.

In the following, the operation of the embodiment shown in FIG. 7, having a liquid switch with a symmetrical branch structure, is explained, making reference to FIGS. 12 and 13. FIGS. 12 and 13 show typical frequency and dispensing protocols run by the device depicted in FIG. 7.

As explained above with respect to FIGS. 3a and 3b, in a symmetrical (inverse-Y structure), the outlet channel is selected by the sense of rotation (and by rotating the rotation body above the critical frequency).

In step 1, a sample volume 222 is supplied to the sample inlet reservoir 144, either during rotation or at rest. The sample can be delivered, making use of the dispenser 160. In the embodiment shown in FIG. 12, delivering of the sample 222 is performed, while the rotation body is at rest. During step 2, the rotation body is accelerated until a frequency of rotation $\omega_1$ above the critical frequency is reached. During this step 2, the channel (at least in the region of the branch between the inlet channel and the outlet channels) is dry, i.e. there is not any liquid volume present.

Due to the centrifugal force caused by the rotation at the frequency $\omega_1$, the sample volume 222 is driven through the inlet channel 116 and the stationary phase 130 and is routed into the first outlet channel 118, step 3. From the outlet channel, the sample buffer flows through the outlet opening 138 into the waste reservoir 146 (not shown in FIG. 12). While maintaining the spinning frequency, a wash buffer volume 224 is dispensed "on-the-fly", making use of the contact-free dispenser 150. The wash buffer is driven through the inlet channel 116 and the stationary phase 130 and is routed into the first outlet channel 118, step 4. Finally, the wash buffer reaches the waste reservoir 146.

After the stationary phase 130 and the branch 122 is centrifuged into a dry state, the sense of rotation is reversed, step 5. To be more specific, the rotation of the rotation body is changed to a rotation in the counter-clockwise direction at a frequency above the critical frequency, $-\omega_1$, for example. As indicated above, during step 5, the channels (at least the channel region including the branch 122) are dry, i.e. free of liquid volume. After surpassing the frequency threshold in the reverse direction, an elution buffer volume 226 is dispensed, making use of the dispenser 150. Alternatively, a separate dispenser could be used to dispense the elution buffer into the same reservoir into which the wash buffer is dispensed, or in a separate reservoir associated with the elution buffer. Due to the rotation at the frequency $-\omega_1$, the elution buffer 226 is driven through the inlet channel 116 and the stationary phase 130 and is routed, i.e. switched, into the outlet channel 120, step 6. From there, the elution buffer may be ejected into the receiving vessel 156. Step 6 is continued until the stationary phase and the channel structure are centrifuged into a dry state. Thereupon, processing of a further sample can be started.

An alternative frequency-dispense protocol for a symmetric branch structure, where dispensing is exclusively performed, while the rotation body is at rest, is shown in FIG. 13. Steps 1 to 3 correspond to steps 1 to 3 described above with respect to FIG. 12. Step 3 is continued until the channel structure (at least in the region of the branch) is dry. Thereupon, rotation of the rotation body is stopped, step 3a. While the rotation body is at rest, the wash buffer volume 224 is dispensed, step 4. In step 5, the rotation body is, again, accelerated to a rotation frequency above the critical frequency, $\omega_1$, for example. Due to the centrifugal force caused by the rotation, the wash buffer volume 224 is driven through the inlet channel 116, the stationary phase 130 and is routed into the outlet channel 118, step 6. Step 6 is continued until the channel structure is dry.

Thereupon, the rotation of the rotation body is stopped again, step 6. While the rotation body is at rest, the elution buffer volume 226 is dispensed, step 8. After dispensing of the elution buffer volume has been finished, the rotation body is accelerated in the reverse sense until a frequency, above the threshold frequency, is reached, for example $-\omega_1$, step 9. In step 10, the elution buffer 226 is driven through the channel structure, as explained above with respect to step 6 of FIG. 12.

The frequency-dispense protocol described above with respect to FIG. 13 can be implemented in applications, in which the "on-the-fly" dispensing through the inlet during rotation may be disadvantageous. In particular, for dispensing at rest, also contact-dispensing methods could be used.

Standard centrifuges are not always capable of changing the sense of rotation. In combination with centrifuges not capable of changing the sense of rotation, a liquid switch, having an asymmetrical branch from the inlet channel into the outlet channels, can be used.

FIG. 14 shows a frequency-dispense protocol, where an asymmetric branch is used to implement a switch, which directs the liquid through the straight channel 52 (FIG. 14) for low frequencies of rotation. The sense of rotation (in FIG. 14 counter-clockwise) is chosen, such that the Coriolis force has components in the direction of the inclined outlet channel 54. Above a frequency threshold, the Coriolis force directs the flow into this outlet channel 54.

In a step 1, a sample volume 230 is dispensed into a reservoir connected to the inlet channel 20. Alternatively, the sample buffer could be dispensed during rotation of the rotation body at a frequency, which is low when compared to the frequency threshold explained above with respect to FIGS. 4a and 4b. At step 2, the rotation body is accelerated to a rotation frequency $\omega_{low}$, which is low when compared to the critical frequency. Thus, by centrifugal force, the sample buffer is driven through the inlet channel 20 and the stationary phase 30 and is routed through the first outlet channel 52, step 3. From the first outlet channel 52, the sample buffer may be driven into a waste reservoir.

During a step 4, a wash buffer volume 232 is dispensed and driven through the inlet channel 20, the stationary phase 30 and routed into the first outlet channel 52 by centrifugal force. From the outlet channel 52, the wash buffer may be driven into a waste reservoir.

The centrifugation of step 4 is continued until the channel structure is dry. Then, in a step 5, the rotation body is accelerated to a frequency $\omega_{high}$ above the threshold frequency. Then, in step 6, an elution buffer volume 234 is dispensed. By centrifugal force, the elution buffer is driven through the inlet channel 20 and the stationary phase 30 and is routed into the second outlet channel 52 by the Coriolis force. From the outlet channel 54, the elution buffer can be ejected into a receiving vessel.

The processing of a further sample can be started as soon as the whole dispensed elution buffer volume has been centrifuged through the channel structure in step 6, and, therefore, the channel structure is dry.

The frequency-dispensed protocols explained above can be obtained under control of the controller 112 controlling the driving means 104 and the dispensers 150 and 160. It can be seen that the control is such that during respective steps in which the rotation of the rotation body changes, the channel structure (or at least the region including the branch between the inlet channel and the outlet channels) is dry. Thus, it is ensured that the respective liquid volumes can be routed into one of the two outlet channels in a defined manner. In other words, during switching intervals, during which a defined routing cannot be obtained, the channel structures are maintained liquid-volume free.

In the above embodiments, the addressing of a selected outlet channel by the sense of rotation and the frequency of rotation or the frequency of rotation only have been explained. In a similar manner, switching to a distinct outlet, which is addressed by the sense of rotation and the rotational acceleration or the rotational acceleration only, can be obtained. In this regard, the rotation body has to be subjected to a rotational acceleration in a first or a second sense above a rotational acceleration threshold, while a liquid volume passes a branch into a first and second outlet channel in order to route the liquid volume into the first or the second outlet channel (for a symmetrical structure). In case of an asymmetrical structure, the rotation body has to be subjected to a rotational acceleration below a given rotational acceleration to route the liquid volume into a first channel and has to be subjected to a rotational acceleration above a rotational acceleration threshold in order to route the liquid volume into a second outlet channel.

Referring to the preferred embodiment of the invention, a structure has been described in which the inlet channel is connected to two reservoirs, while one or two dispensers are provided for dispensing liquid volumes into the reservoirs. However, it is clear for a man of ordinary skill that a different number of reservoirs can be fluidically connected to the inlet of the inlet channel and that another number of dispensers can be used in order to dispense liquid volumes into the reservoirs. For example, one dispenser can be provided for each annular reservoir, so that the dispenser does not have to be repositioned with respect to the reservoir during operation. Alternatively, one dispenser can be provided for a number of annular reservoirs, so that the dispenser has to be repositioned during operation. Moreover, more than one dispenser can be provided for a reservoir in order to deliver different liquid volumes to the same reservoir. Although rotationally symmetrical annular reservoirs have been described with respect to the preferred embodiments of the invention, non-rotationally reservoirs may be provided and a rotational symmetry may be provided by other structures, which do not form reservoirs. The continuous annular reservoirs according to the preferred embodiments of the invention permit a delivery of liquid volumes without synchronization between the position of the rotation body and the dispenser action. Other forms of reservoirs may be provided, which require synchronization between the position of the rotation body and the operation of the dispensers.

FIG. 5 also reveals that not only a binary switch, but also a continuous switch can be realized with the system, which splits the incoming flow according to the sense of rotation, the frequency of rotation and/or the rotational acceleration among the outlets. In principle, also non-contact dispensers and dispensers which are manually actuated can be used, in particular when dispensing while the channel is at rest.

As it is explained above, the system is preferably controlled such that the channel structure, i.e. in particular the stationary phase and the branch, are dry while the frequency of rotation changes. Generally, drying the stationary phase is to be conducted when the outlets are changed only in order to avoid cross contaminations. It is not necessary for the stationary phase to totally dry between the delivery of the sample buffer and the wash buffer. Drying of the channel structure can be obtained by additional centrifugation steps, for example.

In preferred embodiments of the invention, a contact-free dispenser is provided. Alternatively, the invention could make use of a dispenser having a dispensing tip dipping into liquid while rotating the rotation body. Moreover reservoirs of the rotation body could be filled while the rotation body is at rest and in contact with the dispenser.

While this invention has been described in terms of several preferred embodiments, there are alterations, permutations and equivalents, which fall within the scope of this invention. It should also be noted that there are many alternative ways of implementing methods and compositions of the present invention. It is therefore intended that the following appended claims be interpreted as including all such alterations, permutations and equivalents as fall within the true spirit and scope of the present invention.

What is claimed is:

1. A liquid-handling apparatus having a liquid switch, the liquid switch comprising:
 a rotation body rotatable around a rotation axis;
 a first channel formed in the rotation body and, in a branching area, branching into a second channel and a third channel formed in the rotation body;
 wherein the first, second and third channels are adapted for a centrifugal liquid flow therethrough upon rotation of the rotation body,
 wherein the channels are adapted to route a liquid volume from the first channel into one of the second channel and the third channel, dependent on at least one selected from the group comprising a frequency of rotation, a sense of rotation and an acceleration of rotation of the rotation body,
 wherein a portion of the first channel running into the branching area extends in a first direction, wherein a portion of the second channel running into the branching area extends in a second direction, wherein a portion of the third channel running into the branching area extends in a third direction, and wherein the angle between the first and second directions is identical but opposite to the angle between the first and third directions.

2. The liquid-handling apparatus of claim 1, wherein first channel branches into the second and third channels at a symmetric branch, and wherein the channels are adapted to route a liquid volume from the first channel to the second channel when the rotation body rotates in a first sense of rotation at a frequency of rotation above a given frequency and to route a liquid volume from the first channel to the third channel when the rotation body rotates in a second sense of rotation at a frequency of rotation above the given frequency.

3. The liquid-handling apparatus of claim 1, further comprising at least one dispensing unit adapted to dispense to an inlet of the first channel a sequence of a first liquid volume to be routed to the second channel and a second liquid volume to be routed to the third channel.

4. The liquid-handling apparatus of claim 3, comprising a drive adapted to rotate the rotation body and a controller adapted to control the drive to rotate the rotation body such that a liquid volume is routed from the first channel into the second channel or is routed from the first channel into the third channel.

5. The liquid-handling apparatus of claim 4, wherein the second channel and the third channel branch from the first channel in different directions and wherein the controller is adapted to control the drive such that
in a first phase, the rotation body is rotated in a first sense of rotation at a frequency of rotation above a given frequency to route a first liquid volume into the second channel; and
in a second phase, the rotation body is rotated in a second sense of rotation at a frequency of rotation above the given frequency to route a second liquid volume into the third channel.

6. The liquid-handling apparatus of claim 3, wherein the rotation body comprises at least one reservoir fluidically connected to the inlet of the first channel and wherein the dispensing unit is a stationary dispensing unit and is adapted to dispense liquid volumes into the at least one reservoir in a contact-free manner.

7. The liquid-handling apparatus of claim 6, wherein the at least one reservoir is rotationally symmetrical with respect to the rotation axis of the rotation body.

8. The liquid-handling apparatus of claim 7, wherein the at least one reservoir comprises an opening, which is continuously accessible during rotation of the rotation body and through which liquid can be dispensed by the stationary dispensing unit such that the timing of dispensing has not to be synchronized with the azimuthal position of the rotation body during rotation thereof or at rest.

9. The liquid-handling apparatus of claim 1, wherein an outlet of at least one of the second and third channels is adapted such that a liquid volume routed through the corresponding channel can exit the outlet in a free jet.

10. The liquid-handling apparatus of claim 9, wherein a receiving reservoir is provided adapted in order to receive the free jet, wherein the receiving reservoir is mounted for rotation with the rotation body by a bearing such that a liquid surface in the receiving reservoir is aligned perpendicular to the resulting force of the centrifugal force and gravity.

11. The liquid-handling apparatus of claim 1, further comprising at least one receiving reservoir adapted to receive a respective liquid volume routed through at least one of the second channels and the third channels.

12. The liquid-handling apparatus of claim 11, wherein the receiving reservoir is provided on the rotation body and is adapted such that rotational symmetry of the rotation body is maintained.

13. The liquid-handling apparatus of claim 1, comprising a plurality of liquid switches formed in the rotation body, the channels of which are adapted for a centrifugal liquid flow therethrough in a parallel operation.

14. The liquid-handling apparatus of claim 1, further comprising a stationary phase embedded in the first channel.

15. The liquid-handling apparatus according to claim 14, wherein the stationary phase is adapted to perform nucleic acid extractions, filtrations or chromatographic separations on the sample solution.

16. The liquid-handling apparatus of claim 14, further comprising at least one dispensing unit to deliver volumes of liquid to an inlet of the first channel, a drive adapted to controllably rotate the rotation body and a controller adapted to control the at least one dispensing unit and the drive, such that
in a first phase, a volume of sample solution is driven through the stationary phase and the rotation body is rotated so that the sample solution, which has passed the stationary phase, is routed into the second channel;
in a second phase, a volume of wash buffer is driven through the stationary phase and the rotation body is rotated, so that the wash buffer, which has passed the stationary phase, is routed into the second channel; and
in a third phase, a volume of elution buffer is driven through the stationary phase and the rotation body is rotated, so that the elution buffer, which has passed the stationary phase, is routed into the third channel.

17. The liquid-handling apparatus of claim 16, wherein the rotation body comprises at least one reservoir fluidically connected to the inlet of the first channel.

18. The liquid-handling apparatus of claim 17, wherein the controller is adapted to control the dispensing unit, such that
in a fourth phase, prior to the first phase, the volume of sample solution is delivered into one of the at least one reservoirs;
in a fifth phase, between the first phase and the second phase, the volume of wash buffer is dispensed in one of the at least one reservoirs;
in a sixth phase, between the second phase and the third phase, the volume of elution buffer is dispensed in one of the at least one reservoir.

19. The liquid-handling apparatus of claim 18, wherein the the second channel and the third channel branch from the first channel in different directions and wherein the controller is adapted to control the drive such that
in the first and second phases, the rotation body is rotated in a first sense of rotation at a frequency of rotation above a given frequency; and
in the third phase, the rotation body is rotated in a second sense of rotation at a frequency of rotation above the given frequency.

20. The liquid-handling apparatus of claim 19, wherein the controller is adapted to control the drive, such that
in the fourth phase, the rotation body is not rotated, in the fifth phase, the rotation body is rotated in the first sense of rotation at a frequency above the given frequency; and
in the sixth phase, the rotation body is rotated in the second sense of rotation at a frequency above the given frequency.

21. The liquid-handling apparatus of claim 19, wherein the controller is adapted to control the drive, such that the rotation body is not rotated in the fourth, fifth and/or sixth phases.

22. A liquid-handling apparatus having a liquid switch, the liquid switch comprising:
a rotation body rotatable around a rotation axis;
a first channel, a second channel and a third channel formed in the rotation body, wherein, in a branching area, the second channel and the third channel run into the first channel;
wherein the first, second and third channels are adapted for a centrifugal liquid flow thereth rough upon rotation of the rotation body,
wherein the channels are adapted to route a liquid volume from the first channel into one of the second channel and the third channel, dependent on at least one selected from the group comprising a frequency of rotation, a sense of rotation and an acceleration of rotation of the rotation body,
wherein a portion of the first channel running into the branching area extends in a first direction, wherein a portion of the second channel running into the first channel extends in a second direction, wherein a portion of the third channel running into the first channel extends in a third direction, and wherein an angle between the first and second directions is less than an angle between the first and third directions.

23. The liquid-handling apparatus of claim 22, wherein the first channel branches into the second and third channels at an asymmetric branch and wherein the channels are adapted to route a liquid volume from the first channel to the second channel when the rotation body rotates in a first sense of rotation above a given frequency of rotation and to route the liquid volume from the first channel to the third channel when the rotation body rotates in a second sense of rotation or in the first sense of rotation at a frequency below the given frequency.

24. The liquid-handling apparatus of claim 22, wherein the direction of the second channel substantially corresponds to the direction of the first channel and wherein the directions of the first channel and the third channel comprise an angle therebetween.

25. The liquid-handling apparatus of claim 22, comprising at least one dispensing unit adapted to dispense a sequence of a first liquid volume to be routed to the second channel and a second liquid volume to be routed to the third channel to an inlet of the first channel, a drive adapted to rotate the rotation body, and a controller adapted to control the drive to rotate the rotation body such that a liquid volume is routed from the first channel into the second channel or is routed from the first channel into the third channel, wherein the first channel branches into the second and third channels asymmetrically and wherein the controller is adapted to control the drive, such that
in a first phase, the rotation body is rotated in a first sense of rotation at a frequency below a given frequency to route a first liquid volume into the second channel; and
in a second phase, the rotation body is rotated in the first sense of rotation at a frequency above the given frequency to route a second liquid volume into the third channel.

26. The liquid-handling apparatus of claim 25, wherein the controller is adapted to control the at least one dispensing unit and the drive, so that the branching from the first channel to the second and third channel is essentially free of a liquid volume, while the rotation of the rotation body is changed.

27. The liquid-handling apparatus of claim 22,
further comprising a stationary phase embedded in the first channel,
further comprising at least one dispensing unit to deliver volumes of liquid to an inlet of the first channel, a drive adapted to controllably rotate the rotation body and a controller adapted to control the at least one dispensing unit and the drive, such that
in a first phase, a volume of sample solution is driven through the stationary phase and the rotation body is rotated so that the sample solution, which has passed the stationary phase, is routed into the second channel;
in a second phase, a volume of wash buffer is driven through the stationary phase and the rotation body is rotated, so that the wash buffer, which has passed the stationary phase, is routed into the second channel; and
in a third phase, a volume of elution buffer is driven through the stationary phase and the rotation body is rotated, so that the elution buffer, which has passed the stationary phase, is routed into the third channel,
wherein the rotation body comprises at least one reservoir fluidically connected to the inlet of the first channel,
wherein the controller is adapted to control the dispensing unit, such that
in a fourth phase, prior to the first phase, the volume of sample solution is delivered into one of the at least one reservoirs;
in a fifth phase, between the first phase and the second phase, the volume of wash buffer is dispensed in one of the at least one reservoirs; and
in a sixth phase, between the second phase and the third phase, the volume of elution buffer is dispensed in one of the at least one reservoir,
wherein the first channel branches into the second and third channels asymmetrically and wherein the controller is adapted to control the drive, such that
in the first and second phases, the rotation body is rotated in a first sense of rotation at a frequency below a given frequency; and
in the third phase, the rotation body is rotated in the first sense of rotation at a frequency above the given frequency.

28. The liquid-handling apparatus of claim 27, wherein the controller is adapted to control the drive, such that
in the fourth phase, the rotation body is not rotated or rotated in the first sense of rotation at a frequency below the given frequency;
in the fifth phase, the rotation body is rotated in the first sense of rotation at a frequency below the given frequency, and
in the sixth phase, the rotation body is rotated in the first sense of rotation at a frequency above the given frequency.

29. The liquid-handling apparatus of claim 22,
further comprising a stationary phase embedded in the first channel,
further comprising at least one dispensing unit to deliver volumes of liquid to an inlet of the first channel, a drive adapted to controllably rotate the rotation body and a controller adapted to control the at least one dispensing unit and the drive, such that
in a first phase, a volume of sample solution is driven through the stationary phase and the rotation body is rotated so that the sample solution, which has passed the stationary phase, is routed into the second channel;
in a second phase, a volume of wash buffer is driven through the stationary phase and the rotation body is rotated, so that the wash buffer, which has passed the stationary phase, is routed into the second channel; and in a third phase, a volume of elution buffer is driven through the stationary phase and the rotation body is rotated, so that the elution buffer, which has passed the stationary phase, is routed into the third channel, wherein the rotation body comprises at least one reservoir fluidically connected to the inlet of the first channel, wherein the controller is adapted to control the dispensing unit, such that in a fourth phase, prior to the first phase, the volume of sample solution is delivered into one of the at least one reservoirs;

in a fifth phase, between the first phase and the second phase, the volume of wash buffer is dispensed in one of the at least one reservoirs; and in a sixth phase, between the second phase and the third phase, the volume of elution buffer is dispensed in one of the at least one reservoir, wherein the first channel branches into the second and third channels asymmetrically and wherein the controller is adapted to control the drive, such that in the first and second phases, the rotation body is rotated in a first sense of rotation at a frequency above a given frequency, and in the third phase, the rotation body is rotated in the first sense of rotation at a frequency below the given frequency.

30. A method for handling liquid, comprising:

delivering a liquid volume to an inlet of a first channel branching into a second and a third channel in a branching area, wherein a portion of the first channel running into the branching area extends in a first direction, wherein a portion of the second channel running into the branching area extends in a second direction, wherein a portion of the third channel running into the branching area extends in a third direction, and wherein the angle between the first and second directions is identical but opposite to the angle between the first and third directions, wherein the channels are formed in a rotation body and are adapted for a centrifugal fluid flow therethrough upon rotation of the rotation body, and routing the liquid volume from the first channel into one of the second channel and the third channel by rotating the rotation body while controlling at least one of the group comprising a frequency of rotation, a sense of rotation and an acceleration of rotation of the rotation body.

31. The method of claim 30, comprising:

delivering a first liquid volume to the inlet of the first channel;

routing the first liquid volume into the second channel;

delivering a second liquid volume to the inlet of the second channel;

routing the second liquid volume into the third channel.

32. The method of claim 31, wherein routing the first liquid volume into the second channel comprises rotating the rotation body in a first sense of rotation at a frequency above a given frequency, and routing the second liquid volume to the third channel comprises rotating the rotation body in a second sense of rotation at a frequency above the given frequency.

33. The method of claim 30, wherein delivering comprises using a dispensing unit to dispense a liquid volume into a reservoir formed in the rotation body and fluidically connected to the inlet of the first channel.

34. The method of claim 30, comprising driving a liquid volume through a stationary phase located in the first channel by centrifugal force.

35. The method of claim 34, comprising in a first phase, driving a volume of sample solution through the stationary phase and rotating the rotation body, so that the sample solution, which has passed the stationary phase, is routed into the second channel, in a second phase, driving a volume of wash buffer through the stationary phase and rotating the rotation body, so that the wash buffer, which has passed the stationary phase, is routed into the second channel, in a third phase, driving a volume of elution buffer through the stationary phase and rotating the rotation body, so that the elution buffer, which has passed the stationary phase, is routed into the third channel.

36. The method of claim 35, comprising in a fourth phase, prior to the first phase, delivering the volume of sample solution into one of at least one reservoir;

in a fifth phase, between the first phase and the second phase, dispensing the volume of wash buffer in one of the at least one reservoir, and in a sixth phase, between the second phase and the third phase, dispensing the volume of elution buffer in one of the at least one reservoir.

37. The method of claim 36, wherein the second channel and the third channel branches from the first channel in different directions, and wherein in the first and second phases, the rotation body is rotated in a first sense of rotation at a frequency of rotation above a given frequency, and in the third phase, the rotation body is rotated in a second sense of rotation at a frequency of rotation above the given frequency.

38. The method of claim 37, wherein in the fourth phase, the rotation body is not rotated;

in the fifth phase, the rotation body is rotated in the first sense of rotation at a frequency above the given frequency, and in the sixth phase, the rotation body is rotated in a second sense of rotation at a frequency above the given frequency.

39. The liquid-handling apparatus according to claim 37, wherein the rotation body is not rotated in the fourth, fifth and sixth phases.

40. A method for handling liquid, comprising:

delivering a liquid volume to an inlet of a first channel, wherein, in a branching area, a second and a third channel run into the first channel, wherein a portion of the first channel running into the branching area extends in a first direction, wherein a portion of the second channel running into the first channel extends in a second direction, wherein a portion of the third channel running into the first channel extends in a third direction, and wherein an angle between the first and second directions is less than an angle between the first and third directions, and wherein the channels are formed in a rotation body and are adapted for a centrifugal fluid flow therethrough upon rotation of the rotation body, and routing the liquid volume from the first channel into one of the second channel and the third channel by rotating the rotation body while controlling at least one of the group comprising a frequency of rotation, a sense of rotation and an acceleration of rotation of the rotation body.

41. The liquid-handling apparatus of claim 40, comprising
driving a liquid volume through a stationary phase located in the first channel by centrifugal force,
wherein the first channel branches into the second and third channels asymmetrically and wherein
in the first and second phases, the rotation body is rotated in a first sense of rotation at a frequency above a given frequency, and
in the third phase, the rotation body is rotated in the first sense of rotation at a frequency below the given frequency.

42. The liquid-handling apparatus of claim 40, comprising
driving a liquid volume through a stationary phase located in the first channel by centrifugal force,
in a first phase, driving a volume of sample solution through the stationary phase and rotating the rotation body, so that the sample solution, which has passed the stationary phase, is routed into the second channel,
in a second phase, driving a volume of wash buffer through the stationary phase and rotating the rotation body, so that the wash buffer, which has passed the stationary phase, is routed into the second channel,
in a third phase, driving a volume of elution buffer through the stationary phase and rotating the rotation body, so that the elution buffer, which has passed the stationary phase, is routed into the third channel,
in a fourth phase, prior to the first phase, delivering the volume of sample solution into one of at least one reservoir;
in a fifth phase, between the first phase and the second phase, dispensing the volume of wash buffer in one of the at least one reservoir, and
in a sixth phase, between the second phase and the third phase, dispensing the volume of elution buffer in one of the at least one reservoir,
wherein the first channel branches into the second and third channels asymmetrically and wherein
in the first and second phases, the rotation body is rotated in a first sense of rotation at a frequency below a given frequency, and
in the third phase, the rotation body is rotated in the first sense of rotation at a frequency above the given frequency.

43. The liquid-handling apparatus of claim 42, wherein
in the fourth phase, the rotation body is not rotated or rotated in the first sense of rotation at a frequency below the given frequency;
in the fifth phase, the rotation body is rotated in the first sense of rotation at a frequency below the given frequency; and
in the sixth phase, the rotation body is rotated in the first sense of rotation at a frequency above the given frequency.

44. The method of claim 40, wherein
routing the first liquid volume to the second channel comprises rotating the rotation body in a first sense of rotation at a frequency below a given frequency, and
routing the second liquid volume into the third channel comprises rotating the rotation body in the first sense of rotation at a frequency above the given frequency.

* * * * *